United States Patent
Goledzinowski et al.

(10) Patent No.: US 6,627,444 B1
(45) Date of Patent: Sep. 30, 2003

(54) METHOD AND SOLID PHASE CALIBRATION SAMPLE FOR CALIBRATION OF ANALYTICAL INSTRUCTIONS

(75) Inventors: Maciej Goledzinowski, Mississauga (CA); Ludmilla Danylewych-May, North York (CA); John Henry Davies, Mississauga (CA)

(73) Assignee: Smiths Detection - Toronto Ltd., Mississauga (CA)

( * ) Notice: Subject to any disclaimer, the term of this patent is extended or adjusted under 35 U.S.C. 154(b) by 367 days.

(21) Appl. No.: 09/633,901

(22) Filed: Aug. 7, 2000

(51) Int. Cl.[7] .................... G01N 31/00; G01N 21/77
(52) U.S. Cl. ............... 436/8; 436/169; 436/173; 436/181; 422/56; 422/58; 422/69; 250/281; 250/282; 250/288
(58) Field of Search ................... 436/8, 165, 169, 436/173, 181; 422/56, 58, 68.1, 69; 250/281, 282, 288; 356/326; 73/863.21, 863.12, 863.23, 863.31, 864.71

(56) References Cited

U.S. PATENT DOCUMENTS

| | | | | |
|---|---|---|---|---|
| 4,698,071 A | * | 10/1987 | Elias .................... | 95/109 |
| 5,092,217 A | * | 3/1992 | Achter et al. .............. | 86/1.1 |
| 5,405,781 A | | 4/1995 | Davies et al. .............. | 436/52 |
| 5,425,263 A | * | 6/1995 | Davies et al. .............. | 73/28.05 |
| 5,493,890 A | * | 2/1996 | Dussault et al. ........... | 73/1.06 |
| 5,529,686 A | * | 6/1996 | Hagen et al. ............ | 210/198.2 |
| 5,595,649 A | * | 1/1997 | Markell et al. .......... | 210/198.2 |
| 5,741,984 A | * | 4/1998 | Danylewych-May et al. .............. | 73/864.71 |
| 5,796,099 A | | 8/1998 | Jackson ................ | 250/286 |
| 5,859,375 A | * | 1/1999 | Danylewych-May et al. .............. | 73/864.71 |
| 5,866,795 A | | 2/1999 | Wang et al. ............. | 73/1.36 |
| 5,988,002 A | * | 11/1999 | Danylewych-May et al. .............. | 73/864.71 |
| 6,446,514 B1 | * | 9/2002 | Danylewych-May et al. .............. | 73/863.21 |

FOREIGN PATENT DOCUMENTS

| | | | |
|---|---|---|---|
| CA | 2190070 | * | 11/1996 |
| EP | 447158 | * | 9/1991 |

* cited by examiner

Primary Examiner—Maureen M. Wallenhorst
(74) Attorney, Agent, or Firm—Bereskin & Parr

(57) ABSTRACT

A method and a solid phase calibrant are provided suitable for use by untrained personnel to calibrate an analytical instrument under field conditions away from a laboratory. Filter discs or other suitable substrates are impregnated, by the process of adsorption, with solutions of known concentrations of analytes and chromatographic phase materials, such as polymers, in suitable solvents. The substrate material is selected to be chemically inert and to not negatively interact with the analytes, the calibration process, or the analytical instrumentation. The polymers cause the analyte to adhere to the substrate until the solution is desorbed by heating, so that the impregnated substrates form stable calibration solutions in solid phase which can be easily and reliably stored, transported, and used by operators with minimal training. The substrate is preferably contained in a card holder which can be easily inserted into and preferably mate with an inlet for the analytical instrument. Within the instrument, the solid phase calibrant is desorbed by heating the substrate to release a standardized amount of analyte calibrant into the instrument. The calibration technique is particularly suitable for ion mobility spectrometers which detect explosive or narcotic materials.

40 Claims, 1 Drawing Sheet

METHOD AND SOLID PHASE CALIBRATION SAMPLE FOR CALIBRATION OF ANALYTICAL INSTRUCTIONS

FIELD OF THE INVENTION

The present invention relates to the field of analytical chemistry and in particular to a method and calibration sample for calibrating analytical instruments with a standard solution.

BACKGROUND OF THE INVENTION

Analytical instruments, such as ion mobility spectrometers, gas chromatographs, mass spectrometers, and the like, are used to measure chemical properties or chemical composition of an analyte sample or of an analyte component in a sample. Calibration of analytical instruments is necessary to ensure the continued accuracy of measurements performed by such devices. The present invention provides a novel and useful means of calibrating a large class of analytical instruments, including ion mobility spectrometers, gas chromatographs, mass spectrometers, and the like, which operate internally in the vapor phase, but are capable of analyzing volatile solids and liquids because they are provided with inlet means in which solid or liquid samples can be heated and the volatile analytes therein converted to vapour which is then drawn into the instrument for analysis. Many of the foregoing class of instruments are used outside the laboratory, and in such cases, it is customary to collect samples using a specialized inert device, such as a wipe, filter or the like, and then to insert the entire collection device, containing the sample, into the instrument for analysis. These sample collection methods are employed because they allow non-technical personnel to easily and rapidly collect and analyze representative, uncontaminated, samples. In one embodiment, the present invention provides calibration standards which closely mimic these sampling devices in appearance and mode of use, with similar advantages to the operator.

The calibration procedures commonly used in the prior art require the use of one or more standard solutions to calibrate the measurement of unknown analyte concentrations. These standard solutions, which are carefully made up, under controlled laboratory conditions, so as to contain precisely known concentrations of an analyte.

Several methods of calibrating instruments using standard solutions are well known. The working curve calibration method, for example, effectively creates a plot of the analytical signal from the instrument as a function of analyte concentration, i.e. the response of the instrument. This plot is obtained by measuring the signal from a series of standards of known concentrations. The working curves may then be used to determine the concentration of an unknown analyte sample. Similarly, the standard addition calibration procedure is performed by dividing an unknown sample into two portions, and adding a known amount of the analyte under measurement to one of the portions (also known as "spiking" that portion). Both portions of the unknown sample are then analyzed and the difference in responses is due to the additional amount of analyte added to the one portion. This difference thereby provides a calibration point to determine the analyte concentration in the original sample.

Some analytical instruments, particularly those intended for field use by non-technical personnel, do not provide a numeric measure of the amount of analyte in the sample, but only an "Absent/Present" indication. That is, they determine only that the amount of analyte in a sample is greater or less than a threshold value. Such instruments may erroneously indicate "Absent" when the amount of analyte is above the threshold (False Negative) or "Present" when the amount is below threshold (False Positive). False Negatives occur when the sensitivity of the instrument decreases. False Positives can be caused by electrical or similar disturbances in the instrument, and also by other components in the sample being mis-classified as analyte. Acceptable performance for instruments of this type is usually defined by specifying two quantities, namely, the smallest amount of analyte (often called the "Minimum Detectable Amount") which should give no False Negatives, and the maximum tolerable fraction of False Positive responses to samples which contain no analyte. A set of calibration standards for such instruments consist of two types of sample, one known to contain the Minimum Detectable Amount of analyte, and a "blank", containing no analyte. Advantageously, the blank contains typical amounts of the other materials normally accompanying the analyte, and of any materials which are known to be potential sources of False Positives.

In prior art calibration procedures, the standard solutions of known analyte concentrations (or calibration solutions) are produced, maintained, and eventually supplied to the instruments in liquid form. During calibration, the premixed standard liquid solutions are either injected directly into an instrument using syringes or are spotted on to substrates and thermally desorbed into instruments.

Analytical instruments must often be taken into the field to perform in situ measurements. For example, this may be required for soil or water environmental analyses at contaminated sites, for environmental control in oil refineries, for petrochemical processes, for checking contamination at land fill sites, or for checking for drugs and explosives at customs or border stations. In these situations, a more practical and robust calibration means suitable for operation in these environments is highly desirable. Furthermore, field based analytical instrumentation is being increasingly used by environmental specialists, site cleanup and remedial teams, security or customs agents engaged in drug and explosive interdiction, and other similar individuals. In addition to the absence of controlled laboratory environment, this means that sensitive analytical instruments must be operated and calibrated by individuals who are not trained as analytical technicians or chemists (e.g. customs officers, law enforcement, or security agents screening for drugs and explosives). As a result, a simple and easy calibration technique is also required.

In all these circumstances, conditions are not suitable for the storage, transportation, handling, and accurate dispensing of solutions in liquid form. Consequently, there is a genuine need for a simple, practical, and quick calibration technique which provides a high level of measurement accuracy, especially for instruments which are operated under field conditions away from laboratories and by individuals who are, chemically or analytically speaking, unskilled.

SUMMARY OF THE INVENTION

It is an object of the present invention to provide an improved method and apparatus for calibration of analytical instruments, particularly instruments which operate under field conditions away from laboratories or other controlled environments and which may be used by persons without significant skills for carrying out such calibrations by the methods of the prior art.

In a first aspect, the present invention provides a method of providing a calibration sample comprising the steps of:
(a) providing a standard solution containing at least an analyte in a known concentration and a chromatographic phase material; and
(b) impregnating a substrate with the standard solution so that the substrate contains the analyte in a solid phase.

Step (a) can include providing a standard solution containing an explosive analyte material. The explosive analyte material can be selected from the group consisting of: 2,4,6-trinitrotoluene, cyclotrimethylenetrinitramine, pentaerythritol tetranitrate, nitroglycerine, ammonium nitrate, cyclo-tetramethylene-tetranitramine, and tetryl.

Alternatively, step (a) can include providing a standard solution containing an analyte which is a drug or a chromatographic phase material which is a polymer. Such a polymer can be selected from the group consisting of: polydimethylsilane, polymethylsilane, polymethylphenylsilane, polyphenylsilane, and Tenac®.

Preferably, step (a) includes providing a standard solution containing at least one of a dopant, a reactant, and a cleansing agent for an ion mobility spectrometer.

The substrate is preferably formed from a material selected from the group consisting of: fiber glass or polytetrafluoroethylene. More preferably, the substrate material is fiber glass and the method further includes the step of baking the substrate prior to the step of impregnating the substrate.

Conveniently, step (b) comprises adsorbing the standard solution into the substrate.

Preferably, the method further comprises the steps of:
(c) forming the impregnated substrate into sheet material;
(d) cutting the sheet material into calibrant pieces; and
(e) positioning the calibrant pieces on a neutral filter.

The method advantageously further comprises the step of housing the substrate in a card holder to facilitate storage and transportation of the impregnated substrate. Preferably, the step of housing the substrate in a card holder includes the steps of inserting the impregnated substrate into a recessed well located on said card holder and press-fitting an assembly over said substrate to retain the substrate in a fixed position.

Another aspect of the present invention provides a method of calibrating an analytical instrument, the method comprising the steps of providing a calibration sample as defined above and further comprising the steps of
(c) inserting the substrate into a desorption region of the analytical instrument; and
(d) heating the substrate to desorb the analyte.

Advantageously, the substrate is porous and the method further includes the step of sweeping a purge of gas through the substrate during the heating of the substrate in step (d).

Yet another aspect of the present invention provides a method of calibrating an analytical instrument comprising the steps of providing a calibration sample as defined above and further comprising the steps of
(c) forming the impregnated substrate into sheet material;
(d) cutting the sheet material into calibrant pieces;
(e) positioning the calibrant pieces on a neutral filter;
(f) inserting the neutral filter into a desorption region of the analytical instrument; and
(g) heating the substrate to desorb the analyte.

Preferably, the method further comprises the step of providing calibrant pieces suitable for generating a low level analytical instrument output to which the device has been conditioned to classify as a false detection.

The objects and advantages of the present invention will be better understood with reference to the remainder of the description and the drawings.

BRIEF DESCRIPTION OF THE DRAWINGS

In the accompanying drawings which illustrate, by way of example, a preferred embodiment of the invention.

DETAILED DESCRIPTION OF THE INVENTION

Figure 1:
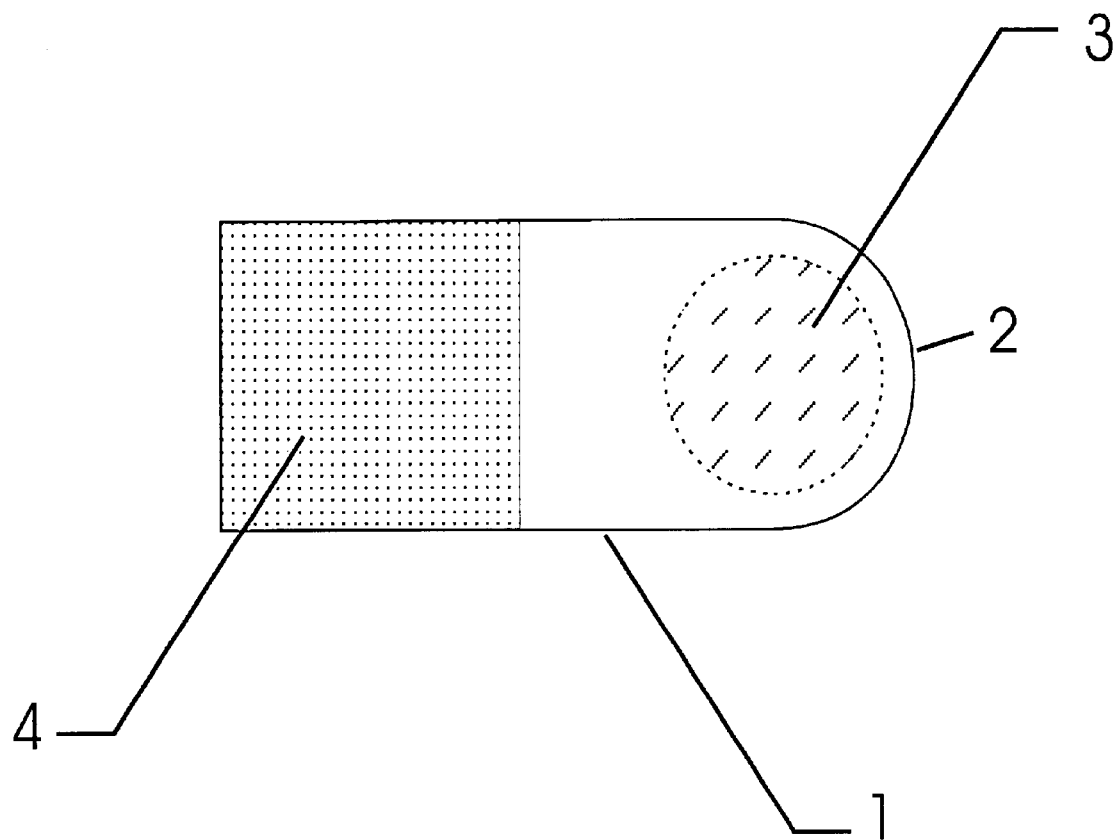
FIG. 1 shows a preferred embodiment of the present invention in the form of a porous lamellar substrate having a first zone which is impregnated with a solid phase calibration solution and a second zone which serves as a handle.

Calibration of analytical instruments has previously been provided through the use of standard solutions which are made up in laboratories and then supplied to instruments in liquid form. These standard liquid solutions are either injected directly into instruments using syringes, or they are spotted onto substrates and thermally desorbed into instruments. Such techniques have become a standard approach for use with gas chromatographs, mass spectrometers and instruments of like kind.

As indicated, the well known techniques of liquid injection of these standard solutions into analytical instruments by spotting premixed liquid calibration solutions or by injecting liquid calibration solutions are generally unsuitable for use under rugged field conditions.

In accordance with the present invention, the requirements of liquid storage, transportation, and injection are eliminated by providing calibration standards in which the analyte is present as a solid phase bonded to the surface of a solid substrate. Calibration standard solutions of the analytes of interest and materials which serve as adsorbing media (as described below) are made up under controlled laboratory conditions and used to impregnate or "spike" appropriate substrates. The added adsorbing materials, which are polymers similar to those used as the stationary phase in gas chromatographs, bind the analyte and make it adhere to the substrate until it is volatilized by heating. Because of the binding action of the polymers, the impregnated substrates form stable calibration samples which can be easily and reliably stored, transported, and used by an operator with minimal training. The chromatographic adsorbing medium is chosen so that, when mixed with the analyte, the resulting suspension or solution can be reproducibly deposited onto the solid absorbing substrate material, either by dipping the substrate into the solution or pipetting the suspension onto the substrate. The added chromatographic material is selected to provide a nondestructive adsorption phase which, upon heating, releases the analyte into a vapor phase without changing it chemically.

Generally the substrates are desorbed at moderate to high temperatures (typically between 100 to 240 C) thereby releasing their analyte in vapor phase into the instrument to be calibrated. Even when heated, the impregnated substrate material should remain neutral with respect to the analyte and chromatographic media, so as to prevent formation of any compounds that would destroy the analyte and/or interfere with analytic process.

Thus, for example, the substrate material may be fiber glass or a polytetrafluorethylene (PTFE) polymer such as Teflon or various combinations of the two, or a cellulose type of material. The substrate may also be baked so that it is preconditioned for adsorption and subsequent desorption of the analyte. These solid phase calibration standards, when thermally desorbed, release pre-determined quantities of calibration analyte into the instrument thereby allowing it to be calibrated for sensitivity and dynamic range and correct rejection of interfering materials. The calibration technique can be conveniently used for calibrating ion mobility spectrometers and other analytical devices.

The preferred embodiment may be better understood with reference to FIG. 1. Substrates 1 are cut from a sheet of porous material which may be fiber glass or polytetrafluorethylene (PTFE) or fiberglass coated with PTFE or cellulose paper, or other material which, when heated to the temperature required to vaporize the analyte, will not react with the analyte nor evolve any material which will interfere with the operation of the instrument to be calibrated. The substrate is shaped and designed to mate, for example in a key-like pattern, with a given class of analytical instrument, so that it is readily, directly, and reproducibly insertable into the desired inlet of that class of analytical instrument. In particular, the size and position of the zone 3 and the shape of the end 2 are such that, when the end 2 is inserted into said inlet, the zone 3 is positioned entirely within the region normally occupied by a sample when it is being analyzed. The shape, size and position of the zone 4 are such that an operator can easily grasp and manipulate the substrate using zone 4 while avoiding contact with zone 3. The thickness and rigidity of the substrate are such that it is self-supporting and can be handled without damage, and the porosity of the substrate is such as to allow air or other gas to be freely aspirated through the substrate in order to entrain thermally-desorbed analyte vapours and transport them into the instrument being calibrated. Known amounts of analyte and a chromatographic polymer are mixed with a suitable solvent to produce solutions or suspensions containing known concentrations of analyte. A known quantity of this solution or suspension is then pipetted onto zone 3 and the solvent allowed to evaporate, leaving a known amount of the analyte firmly bound to the substrate in zone 3.

In another embodiment of the present invention, strips of substrate material are dipped into solutions containing known concentrations of analyte and chromatographic polymer, removed, and dried on racks in an inert atmosphere. These strips then contain a known mass of analyte per unit area, and discs or tokens cut from these treated strips form stable calibration standards, which, when inserted into the inlet of an analytical instrument and heated, will release a known amount of analyte.

Advantageously, as variants of the embodiments described above, calibration standards for False Positives can be made by omitting the analyte. In a further useful variant, the analyte can be replaced by a known amount of a material known to interfere with the analytical process, and such standards can then be used to confirm correct operation of those internal subsystems of the analytical instrument whose specific task it is to compensate for or suppress the undesirable effects of the interferent material.

Furthermore, as will be obvious to those skilled in the art the methods of the present invention may be used to prepare standards containing more than one analyte, or a combination of one or more analytes with one or more potential interferents, in order to provide simple and convenient means to confirming correct operation of analytical instruments used to detect multiple materials in complex matrices.

The above described solid phase calibration sample and calibration method is conveniently suitable for use with the class of instruments known as Ion Mobility Spectrometers (IMS). This is especially true for IMS instruments which use thermal desorption and particularly solid phase collection and desorption. Such an IMS is described in detail in U.S. Pat. No. 5,796,099, the contents of this patent being incorporated herein by reference.

The stability of calibration standards prepared by the method of the present invention was tested for explosive analytes using an IMS. The following explosive analytes were tested: 2,4,6-trinitrotoluene (TNT); cyclotrimethylenetrinitramine or cyclonite (RDX); pentaerythritol tetranitrate (PETN); nitroglycerine (NG); and ammonium nitrate (AN). Each of these explosive analytes was mixed with the polymer polyphenylsilane (PPS), and a token fiber glass filter substrate was then spiked with one of the solutions for testing purposes. In the case of Ammonium Nitrate, a porous, teflon reinforced fiber glass substrate was used. Generally, the fiber glass filters were spiked with explosives/polymer solutions that were equivalent to 1.5 to 10 times the appropriate minimum detection limit of the IMS. The appropriate IMS signal amplitudes were established by depositing pure explosives solutions (at 1.5, 5 and 10 times the detection limit) on the fiber glass filters. The amounts of explosive/polymer solution that generated IMS responses equivalent to 1.5 and 5 times the detection limit were then verified by comparing the signals produced by the explosive/polymer samples to those produced by the samples containing pure analyte. Subsequently, the IMS responses for the filters spiked with explosive/polymer mixture at the level of 1.5 to 10 times the detection limit were measured after approximately 5, 10, and 25 days from the day of spiking.

Table I provides an indication of the percent retention relative to the initially prepared token filters. Two different types of filter storage were used: at room temperature (22° C.) and refrigerated (4° C.). Twenty plasmagrams were measured for each token after 5, 10, and 25 days, and both the maximum IMS amplitude and the cumulative sum of the twenty amplitudes were recorded and compared to the values for filters measured after spiking.

TABLE I

| Explosive/Amount | 22° C. 5 days | | 22° C. 10 days | | 22° C. 25 days | | 4° C. 25 days | |
| --- | --- | --- | --- | --- | --- | --- | --- | --- |
| | Max % | Cum % | Max % | Cum % | Max % | Cum % | Max % | Cum % |
| TNT/0.6 ng | 100 ± 15 | 91 ± 20 | 100 ± 20 | 90 ± 20 | 57 ± 15 | 40 ± 16 | 100 ± 12 | |
| | | | | | | | 100 ± 9 | |
| RDX/1.5 ng | 100 ± 6 | 100 ± 9 | 100 ± 5 | 100 ± 14 | 100 ± 10 | 100 ± 5 | 100 ± 5 | 100 ± 6 |
| PETN/1.5 ng | 100 ± 10 | 100 ± 14 | 100 ± 6 | 100 ± 9 | 88 ± 6 | 98 ± 13 | 92 ± 9 | 91 ± 16 |
| NG/2 NG | 100 ± 9 | 100 ± 11 | 94 ± 10 | 100 ± 10 | 79 ± 16 | 84 ± 10 | 100 ± 9 | 100 ± 9 |
| AN/10 ng[1] | | | | | 89 ± 3 | 74 ± 15 | 100 ± 7 | 90 ± 17 |

[1] Ammonium Nitrate solutions deposited on Teflon-reinforced fibre glass filter.
[2] NG sensitivity filters had to be stored for 2 days after spiking, prior to analysis, in order to obtain stable and reproducible results.

As Table I indicates, retention of all explosives tested is better than 90% after 25 days storage at 4° C. or after 10 days at room temperature. There was some loss of TNT, NG and AN after 25 days at room temperature, but in no case was the amount retained less than 40%. It was also found that, in general, the retention of explosives increases with an increased polarity of polymer phase. This trend was demonstrated by using a class of polymers where polarities were modified by substitution of phenyl groups in place of methyl. The polarity of the polymeric silanes increases in the following order: polydimethylsilane (PDMS) <polymethylsilane (PMS)<polymethylphenylsilane (PMPS) <polyphenylsilane (PPS), and the retention of the explosives on these polymers follows the same progression, and so the use of the PPS polymer with the above explosive analytes is preferable.

Thus, the present invention provides a method for the manufacture of stable, portable calibration standards suitable for use by untrained personnel under field conditions. As mentioned, the substrate material is selected to be chemically inert, to not negatively interact with the analytes used in the calibration process, to be able to withstand the temperatures of desorption, and not in itself provide off-gases which can act as interferences or liberate other trace chemicals that could otherwise interact negatively upon the calibration process or the operation of the instruments. The chromatographic materials are selected for stable adsorption and retention of the analyte at room temperature and efficient release of analyte vapour, without decomposition, at elevated temperature. After evaporation of the solvent, the treated substrates constitute a sample or source of analyte which can be volatilized by heating the filter. In general, the inventors have determined that the amount of analyte released remains relatively stable for at least 22 days when stored at 22° C. and for at least several months when refrigerated.

Solid phase calibration samples according to the present invention may be produced as follows. Solutions containing known concentrations of polymer and analyte are prepared by adding a precisely weighed amount of the polymer to a suitable solvent and combining the resulting solution with concentrated analyte stock solutions to achieve the required concentrations of analyte. For calibration of Ion Mobility Spectrometers for the detection of explosives, the mixtures shown in Table II can be used effectively:

TABLE II

| Explosive Analyte/ Amount | Chromotographic Phase/ Polymer | Solvent |
| --- | --- | --- |
| TNT/1.6 ng | 6.4% PPS | acetone + xylene (2.7:1 v/v) |
| RDX/1.5 ng | 6.1% PPS | acetone + xylene (4:1 v/v) |
| PETN/1.5 ng | 6.7% PPS | acetone + xylene (4:1 v/v) |
| NG/2.0 ng | 2.5% Tenax ® + 2.5% PPS | chloroform + xylene (5:1 v/v) |
| AN/2.0 ng | 6.7% PPS | acetone + xylene (4:1 v/v) |

Fiber glass filters which have been baked for 60 minutes at 180° C. are then spiked with the explosive/polymer solution using an Eppendorf® pipette. The spiked volume is maintained in the range of 1–10 L. If the spiked volume is higher than 5 L, two equal portions of the solution are preferably deposited on the filter in order to avoid the soaking effect and possible loss of the analyte. The pipette tips are changed frequently, for example after a few spikes (in general this will depend on the polymer being used), to avoid deposition of solid polymer phase on the walls of the tip.

It should be noted that while the above discussion has related primarily to the use of an IMS or ion mobility spectrometer for detecting explosives, this is merely by way of example. For instance, other explosives such as cyclo-tetramethylene-tetranitramine (HMX) or tetryl (trinitrophenylmethylnitramine) may also be used as analytes. Furthermore, it will be clear that the present invention applies equally to other types of analyte like drugs or narcotics (e.g. heroine, cocaine, tetrahydrocannabinol (THC), and methamphetamines) and to other types of analytical instruments, such as chemiluminescent detectors, mass spectrometers with solid phase sample inlets, various types of pyrolysis instrumentation, electronic noses, and electrochemical cells.

While preferred embodiments of the present invention have been described, the embodiments disclosed are illustrative and not restrictive, and the invention is intended to be defined by the appended claims.

What is claimed is:

1. A method of providing a calibration sample for an analytical instrument comprising the steps of:
    (a) providing a standard solution containing at least an analyte in a known concentration and a chromatographic phase material; and
    (b) impregnating a substrate with the standard solution so that the substrate contains the analyte in a solid phase.

2. A method as claimed in claim 1 wherein step (a) includes providing a standard solution containing an explosive analyte material.

3. A method as claimed in claim 2 wherein the explosive analyte material is selected from the group consisting of: 2,4,6-trinitrotoluene, cyclotrimethylenetrinitramine, pentaerythritol tetranitrate, nitroglycerine, ammonium nitrate, cyclo-tetramethylene-tetranitramine, and tetryl.

4. A method as claimed in claim 1 wherein step (a) includes providing a standard solution containing an analyte which is a drug.

5. A method as claimed in claim 1 wherein step (a) includes providing a standard solution containing a chromatographic phase material which is a polymer.

6. A method as claimed in claim 5 wherein the polymer is selected from the group consisting of: polydimethylsilane, polymethylsilane, polymethylphenylsilane, polyphenylilane, and 2,6-di-phenyl-p-phenylene oxide.

7. A method as claimed in claim 5 wherein the polymer is polyphenylsilane.

8. A method as claimed in claim 1 wherein step (a) includes providing a standard solution containing in addition to said analyte and said chromatograhic phase material at least one of a dopant, a reactant, and a cleansing agent for an ion mobility spectrometer.

9. A method as claimed in claim 1 wherein step (a) includes providing a standard solution containing at least one material which the analytical instrument has been programmed to reject.

10. A method as claimed in claim 9 in which the analytical instrument is an ion mobility spectrometer.

11. A method as claimed in claim 1 further including the step of forming the substrate from a material selected from the group consisting of fiber glass, polytetrafluorethylene, and a combination of fiber glass and polytetrafluorethylene.

12. A method as claimed in claim 11 wherein said substrate material is fiber glass and further including the step of baking the substrate prior to the step of impregnating the substrate.

13. A method as claimed in claim 11 wherein the step of forming the substrate includes the step of forming said substrate into a filter disc.

14. A method as claimed in claim 1 wherein step (b) comprises adsorbing the standard solution into the substrate.

15. A method as claimed in claim 1 further comprising the steps of:
   (c) forming the impregnated substrate into sheet material;
   (d) cutting the sheet material into calibrant pieces; and
   (e) positioning the calibrant pieces on a neutral filter.

16. A method as claimed in claim 15 including providing calibrant pieces having different analytes impregnated therein.

17. A method as claimed in claim 1 further comprising the step of housing the substrate in a card holder to facilitate storage and transportation of the impregnated substrate.

18. A method as claimed in claim 17 wherein the step of housing the substrate in a card holder includes the steps of inserting the impregnated substrate into a recessed well located on said card holder and press-fitting an assembly over said substrate to retain the substrate in a fixed position.

19. A method as claimed in claim 1 further including the step of refrigerating the impregnated substrate to prolong the stability of the standard solution.

20. A method as claimed in claim 1 wherein step (a) comprises dissolving a precisely weighed amount of the chromatographic phase material in a solvent, mixing a portion of the resulting solution with a concentrated stock solution containing the analyte to achieve the standard solution having a required known concentration of the analyte.

21. A method of calibrating an analytical instrument comprising the steps of providing a calibration sample according to the method of claim 1 and further comprising the steps of
   (c) inserting the substrate into a desorption region of the analytical instrument; and
   (d) heating the substrate to desorb the analyte.

22. A method as claimed in claim 21 wherein said substrate is porous and further including the step of sweeping a purge of gas through the substrate during the heating of the substrate in step (d).

23. A method as claimed in claim 21 further comprising the steps of housing the substrate in a card holder and inserting the card holder into an inlet of the analytical instrument, the card holder and the inlet being shaped to mate with one another for conveniently inserting a portion of the card holder having the substrate into the desorption region of the analytical instrument.

24. A method as claimed in claim 23 wherein the analytical instrument is an ion mobility spectrometer.

25. A method of calibrating an analytical instrument comprising the steps of providing a calibration sample according to the method of claim 1 and further comprising the steps of
   (c) forming the impregnated substrate into sheet material;
   (d) cutting the sheet material into calibrant pieces;
   (e) positioning the calibrant pieces on a neutral filter;
   (f) inserting the neutral filter into a desorption region of the analytical instrument; and
   (g) heating the substrate to desorb the analyte.

26. A method as claimed in claim 25 wherein the analytical instrument is an ion mobility spectrometer.

27. A method as claimed in claim 1 wherein step (a) includes providing a standard solution containing at least one of a dopant, a reactant and a cleansing agent for an ion mobility spectometer, and wherein at least one of said dopant, said reactant and said cleansing agent includes said analyte.

28. A method as claimed in claim 1, wherein step (a) includes providing a standard solution containing at least one of a dopant, a reactant and a cleansing agent for an ion mobility spectrometer, and wherein at least one of said dopant, said reactant and said cleansing agent includes said chromatographic phase material.

29. A calibration sample comprising a substrate having a standard solution in a solid phase impregnated thereon, the standard solution containing at least an analyte in a known concentration and a chromatographic phase material.

30. A calibration sample as claimed in claim 29 wherein the analyte is an explosive material.

31. A calibration sample as claimed in claim 30 wherein the explosive analyte is selected from the group consisting of: 2,4,6-trinitrotoluene, cyclotrimethylenetrinitramine, pentaerythritol tetranitrate, nitroglycerine, ammonium nitrate, cyclo-tetramethylene-tetranitramine, and tetryl.

32. A calibration sample as claimed in claim 29 wherein the analyte is a drug.

33. A calibration sample as claimed in claim 29 wherein the chromatographic phase material is a polymer.

34. A calibration sample as claimed in claim 33 wherein the polymer is selected from the group consisting of: polydimethylsilane, polymethylsilane, polymethylphenylsilane, polyphenylsilane, and 2,6-diphenyl-p-phenylene oxide.

35. A calibration sample as claimed in claim 34 wherein the polymer is polyphenylsilane.

36. A calibration sample as claimed in claim 29 wherein the standard solution further contains at least one of a dopant, a reactant, and a cleansing agent for an ion mobility spectrometer.

37. A calibration sample as claimed in claim 29 wherein the substrate is formed from a material selected from the group consisting of fiber glass and polytetrafluorethylene.

38. A calibration sample as claimed in claim 29 wherein the substrate is a filter disc.

39. A calibration sample as claimed in claim 29 wherein the substrate is housed in a card holder to facilitate storage and transportation of the impregnated substrate.

40. A calibration sample as claimed in claim 39 wherein the card holder includes a recessed well therein for receiving the impregnated substrate and an assembly sized to fit over the substrate to retain the substrate in a fixed position.

* * * * *

UNITED STATES PATENT AND TRADEMARK OFFICE
CERTIFICATE OF CORRECTION

PATENT NO.   : 6,627,444 B1
DATED        : September 30, 2003
INVENTOR(S)  : Maciej Goledzinowski, Ludmilla Danylewych-May and John Hendry Davies It is certified that error appears in the above-identified patent and that said Letters Patent is hereby corrected as shown below:

<u>Title page, Item [54] and Column 1, lines 1-4,</u>
Title, reads "METHOD AND SOLID PHASE CALIBRATION SAMPLE FOR CALIBRATION OF ANALYTICAL INSTRUCTIONS" should read
-- METHOD AND SOLID PHASE CALIBRATION SAMPLE FOR CALIBRATION OF ANALYTICAL INSTRUMENTS --

Signed and Sealed this

Sixth Day of April, 2004

JON W. DUDAS
*Acting Director of the United States Patent and Trademark Office*